(12) United States Patent
Umemoto et al.

(10) Patent No.: US 8,888,685 B2
(45) Date of Patent: Nov. 18, 2014

(54) MEDICAL SYSTEM

(71) Applicant: Olympus Medical Systems Corp., Tokyo (JP)

(72) Inventors: Yoshitaka Umemoto, Hachioji (JP); Yasuhiro Okamoto, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/946,582

(22) Filed: Jul. 19, 2013

(65) Prior Publication Data

US 2014/0039254 A1 Feb. 6, 2014

Related U.S. Application Data

(63) Continuation of application No. PCT/JP2012/076273, filed on Oct. 11, 2012.

(30) Foreign Application Priority Data

Feb. 15, 2012 (JP) .................................. 2012-030725

(51) Int. Cl.
*A61B 1/00* (2006.01)
*A61B 1/04* (2006.01)
(Continued)

(52) U.S. Cl.
CPC ........ *A61B 1/00002* (2013.01); *G02B 23/2423* (2013.01); *A61B 17/0218* (2013.01);
(Continued)

(58) Field of Classification Search
CPC ........... A61B 1/00082; A61B 1/00087; A61B 1/00009; A61B 1/00133; A61B 1/005
USPC ......... 600/104, 106, 115, 116, 117, 118, 146, 600/153, 158
See application file for complete search history.

(56) References Cited

U.S. PATENT DOCUMENTS 5,749,830 A * 5/1998 Kaneko et al. ................. 600/160
2002/0165432 A1 * 11/2002 Matsui .......................... 600/145
(Continued)

FOREIGN PATENT DOCUMENTS

EP 1 669 026 A1 6/2006
JP A-2005-103123 4/2005
(Continued)

OTHER PUBLICATIONS

Jan. 8, 2013 International Search Report issued in International Application No. PCT/JP2012/076273 (with translation).

(Continued)

*Primary Examiner* — Anhtuan Nguyen
*Assistant Examiner* — William Chou
(74) *Attorney, Agent, or Firm* — Oliff PLC (57) ABSTRACT

A medical system includes: an endoscope including an insertion portion that can be inserted into a body cavity of a subject, and an image pickup section provided at a distal end portion of the insertion portion; an exclusion section capable of, when the insertion portion is inserted into the body cavity of the subject, excluding a tissue existing around the distal end portion; a computing section that obtains luminance information relating to a luminance of an image picked up by the image pickup section, and determines whether or not the obtained luminance information meets a predetermined condition; a drive section that if a determination result that the luminance information does not meet the predetermined condition is provided, continues an operation to drive the exclusion section, and if a determination result that the luminance information meets the predetermined condition is provided, stops the operation to drive the exclusion section.

6 Claims, 9 Drawing Sheets

(51) Int. Cl.
  *A61B 1/06* (2006.01)
  *G02B 23/24* (2006.01)
  *A61B 1/005* (2006.01)
  *A61B 1/018* (2006.01)
  *A61B 17/02* (2006.01)
  *A61B 17/00* (2006.01)

(52) U.S. Cl.
  CPC ........... *A61B 1/0051* (2013.01); *A61B 1/00009* (2013.01); *A61B 1/0016* (2013.01); *A61B 2017/00296* (2013.01); *A61B 1/018* (2013.01); *G02B 23/2476* (2013.01)
  USPC ............ 600/118; 600/116; 600/117; 600/160

(56) References Cited

U.S. PATENT DOCUMENTS

| | | | |
|---|---|---|---|
| 2005/0124875 A1 | 6/2005 | Kawano et al. | |
| 2005/0165279 A1* | 7/2005 | Adler et al. | 600/181 |
| 2008/0234546 A1* | 9/2008 | Kawano et al. | 600/104 |
| 2008/0242928 A1 | 10/2008 | Kawano et al. | |
| 2009/0287051 A1* | 11/2009 | Itoi | 600/115 |

FOREIGN PATENT DOCUMENTS

| | | |
|---|---|---|
| JP | A-2005-124708 | 5/2005 |
| JP | A-2010-068859 | 4/2010 |
| JP | A-2010-183949 | 8/2010 |
| JP | A-2010-187903 | 9/2010 |
| JP | A-2011-072598 | 4/2011 |
| WO | WO 2005/032370 A1 | 4/2005 |

OTHER PUBLICATIONS

Sep. 2, 2013 Office Action in Japanese Patent Application No. 2013-532007 (with translation).

* cited by examiner

MEDICAL SYSTEM

CROSS REFERENCE TO RELATED APPLICATION

This application is a continuation application of PCT/JP2012/076273 filed on Oct. 11, 2012 and claims benefit of Japanese Application No. 2012-030725 filed in Japan on Feb. 15, 2012, the entire contents of which are incorporated herein by this reference.

BACKGROUND OF THE INVENTION

1. Field of the Invention

The present invention relates to a medical system, and specifically relates to a medical system used for, e.g., observation of the inside of a body cavity.

2. Description of the Related Art

A technique in which when endoscopic observation of the inside of a body cavity of a subject is underway, for example, a tissue or the like existing around a distal end portion of an insertion portion of the endoscope is temporarily moved (from an original position thereof) to ensure a field of view for observing or treating a desired site has conventionally been used.

As an example configuration that can be used for the above technique, a configuration, such as disclosed in Japanese Patent Application Laid-Open Publication No. 2010-187903, in which an expansive member such as a balloon is provided at a distal end portion of an insertion portion of an endoscope has been proposed.

SUMMARY OF THE INVENTION

A medical system according to an aspect of the present invention includes: an endoscope including an insertion portion that can be inserted into a body cavity of a subject, and an image pickup section provided at a distal end portion of the insertion portion; an exclusion section configured to be capable of, when the insertion portion is inserted into the body cavity of the subject, excluding a tissue existing around the distal end portion; a computing section that obtains luminance information relating to a luminance of an image picked up by the image pickup section, and determines whether or not the obtained luminance information meets a predetermined condition; a drive section that if a determination result that the luminance information does not meet the predetermined condition is provided by the computing section, continues an operation to drive the exclusion section, and if a determination result that the luminance information meets the predetermined condition is provided by the computing section, stops the operation to drive the exclusion section.

DETAILED DESCRIPTION OF THE PREFERRED EMBODIMENT

An embodiment of the present invention will be described below with reference to the drawings.

Figure 1:
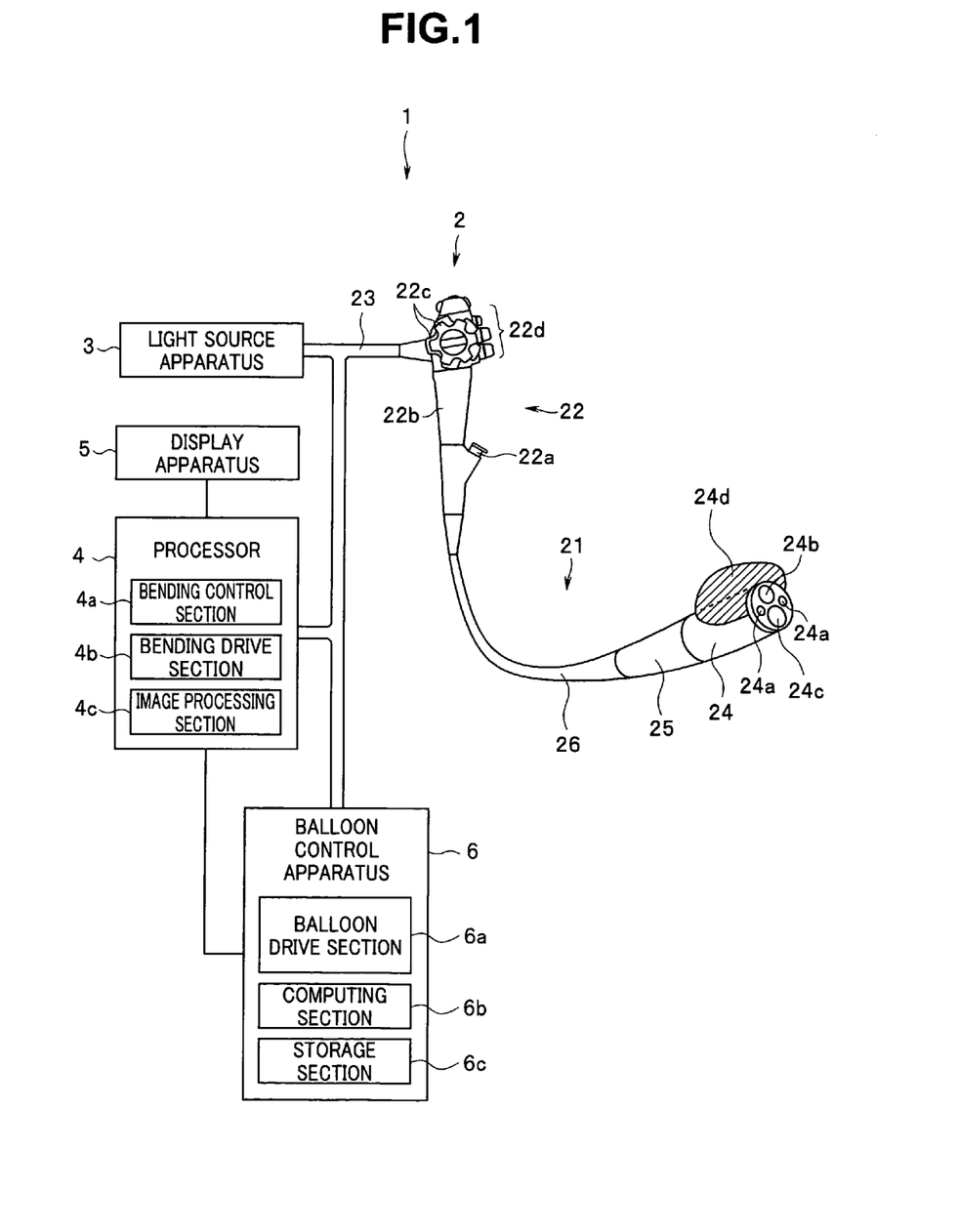
FIG. 1 is a diagram illustrating a configuration of a main part of an endoscope system according to an embodiment of the present invention.

FIGS. 1 to 4 relate to an embodiment of the present invention. FIG. 1 is a diagram illustrating a configuration of a main part of an endoscope system according to an embodiment of the present invention.

As illustrated in FIG. 1, an endoscope system 1 includes: an endoscope 2 capable of picking up an image of an object in a body cavity of a subject to acquire an endoscopic image; a light source apparatus 3 having a function as a supply source of illuminating light for illuminating the object; a processor 4 that performs, e.g., image processing on the endoscopic image acquired by the endoscope 2; a display apparatus 5 capable of displaying, e.g., the endoscopic image subjected to the image processing by the processor 4; and a balloon control apparatus 6 that performs an operation relating to control of a balloon 24d (which will be described later) provided at the endoscope 2.

The endoscope 2 includes an insertion portion 21 having an elongated shape that can be inserted into a body cavity of a subject; an operation portion 22 provided on the rear end side of the insertion portion 21, and a universal cord 23 provided so as to extend out from the operation portion 22. Inside the insertion portion 21, the operation portion 22 and the universal cord 23, a non-illustrated light guide (light guiding member) capable of conveying illuminating light supplied from the light source apparatus 3, and a non-illustrated gas circulation duct (gas circulation channel) used for air feeding/exhaust performed by the balloon control apparatus 6 are inserted.

The insertion portion 21 includes a distal end portion 24, a bending portion 25 and a flexible tube portion 26, which are provided continuously in this order from the distal end side to the rear end side. In other words, the bending portion 25 is provided at least in a part of the insertion portion 21.

In a distal end face of the distal end portion 24, two illumination windows 24a, an objective window 24b and a distal end opening portion 24c are disposed. Furthermore, a balloon 24d is attached to the vicinity of the objective window 24b, at an outer circumferential part of the distal end portion 24.

Furthermore, inside the distal end portion 24, a non-illustrated image pickup section that includes, e.g., optical elements and an image pickup device, and is configured to be capable of picking up an object image entered from the objective window 24b to provide an image (endoscopic image) is provided. In other words, the image pickup section in the distal end portion 24 is disposed on the back side of the objective window 24b.

The balloon 24d having a function as an exclusion section is provided in the vicinity of the image pickup section, at the outer circumferential part of the distal end portion 24.

On the back side of each of the two illumination windows 24a, an end portion on the light exit side of the light guide inserted inside the insertion portion 21.

The distal end opening portion 24c is in communication with a non-illustrated treatment instrument insertion duct (treatment instrument channel) disposed inside the insertion portion 21, and has a shape that enables an elongated treatment instrument inserted from a forceps port 22a (which will be described later) to project ahead of the distal end portion 24.

The balloon 24d includes a soft material such as rubber, and is configured to expand upon supply of a gas to an inner space thereof, and shrink upon discharge of the gas supplied to the inner space. Also, the inner space of the balloon 24d is in communication with one end portion of the gas circulation duct inserted inside the insertion portion 21.

The bending portion 25 includes, e.g., a plurality of bending pieces to which respective end portions of a plurality of wires are attached, and is configured to be capable of changing an orientation of the distal end portion 24 as a result of the bending portion 25 being bent in a direction according to an operation of a bending operation portion 22c (which will be described later) of the operation portion 22.

The operation portion 22 includes the forceps port 22a disposed at a side portion on the distal end side, a grasping portion 22b to be grasped by a surgeon or the like, the bending operation portion 22c provided on the rear end side of the grasping portion 22b, and a scope switch section 22d including a plurality of switches that enable provision of instructions to activate or stop various functions provided by the respective parts of the endoscope system 1.

The forceps port 22a is in communication with a non-illustrated treatment instrument insertion duct disposed inside the insertion portion 21, and has a shape that allows an elongated treatment instrument to be inserted thereto.

The bending operation portion 22c is configured to enable a bending operation for bending the bending portion 25 in a desired direction by a desired amount to be performed, and also to enable an instruction signal according to the bending operation to be outputted to the processor 4 via a signal wire incorporated in the universal cord 23.

In the scope switch section 22d, for example, the plurality of switches such as an automatic control mode switch that enables provision of an instruction to turn on automatic control of the balloon 24d by the balloon control apparatus 6, an air feeding switch that enables provision of an instruction relating to turning-on/off of feeding of a gas to the inner space of the balloon 24d, and an air exhaust switch that enables provision of an instruction relating to turning-on/off of exhaust of a gas in the inner space of the balloon 24d are provided.

In the universal cord 23, the light guide capable of conveying illuminating light supplied from the source apparatus 3, a plurality of signal wires used for transmission/reception of various signals between the endoscope 2, and the processor 4 and the balloon control apparatus 6, and the gas circulation duct used for air feeding/exhaust performed by the balloon control apparatus 6 are incorporated.

Also, at an end portion of the universal cord 23, a plurality of non-illustrated connectors, which are connectable to respective parts of the light source apparatus 3, the processor 4 and the balloon control apparatus 6, are provided.

Inside the connector connected to the light source apparatus 3 from among the respective connectors provided at the end portion of the universal cord 23, an end portion on the light entrance side of the light guide is disposed.

Inside the connector connected to the balloon control apparatus 6 from among the respective connectors provided at the end portion of the universal cord 23, the other end portion of the gas circulation duct, and an end portion of a signal wire that enables detection of an instruction signal outputted according to an operation of the scope switch section 22d are disposed.

In other words, the configuration described above allows illuminating light supplied from the light source apparatus 3 to exit from the two illumination windows 24a via the light guide inserted inside the insertion portion 21, the operation portion 22 and the universal cord 23.

Furthermore, the configuration described above enables the balloon control apparatus 6 to change the state of expansion of the balloon 24d via the gas circulation duct inserted inside the insertion portion 21, the operation portion 22 and the universal cord 23.

The processor 4 includes a bending control section 4a, a bending drive section 4b and an image processing section 4c.

The bending control section 4a includes, e.g., a CPU, and is configured to calculate a bending amount for the bending portion 25 based on an instruction signal outputted according to an operation of the bending operation portion 22c and control the bending drive section 4b according to the calculated bending amount.

The bending drive section 4b includes, e.g., a motor for pulling the respective wires attached to the respective bending pieces in the bending portion 25, and is configured to be capable of bending the bending portion 25 by a bending amount according to control performed by the bending control section 4a.

The image processing section 4c is configured to perform various types of image processing (for example, denoising) on an image (endoscopic image) acquired by the image pickup section in the distal end portion 24 and output the endoscopic image subjected to the image processing to the display apparatus 5 and the balloon control apparatus 6.

The balloon control apparatus 6 includes a balloon drive section 6a, a computing section 6b, and a storage section 6c in which threshold information used for computing performed by the computing section 6b is stored in advance.

The balloon drive section 6a includes, e.g., a pump connectable to the other end portion of the above-described gas circulation duct, and a tank, which is a supply source of a gas to be supplied to the gas circulation duct, and is configured to be capable of performing an operation relating to supply of a gas to the inner space of the balloon 24d (air feeding operation), and an operation relating to exhaust of the gas supplied to the inner space of the balloon 24d (air exhaust operation), respectively.

The balloon drive section 6a performs an air feeding operation according to an instruction signal outputted from the air feeding switch in the scope switch section 22d if the balloon drive section 6a detects that automatic control of the balloon 24d by the balloon control apparatus 6 is not turned on, based on an instruction signal outputted from the scope switch section 22d via the universal cord 23.

The balloon drive section 6a performs an air exhaust operation according to an instruction signal outputted from the air exhaust switch in the scope switch section 22d if the balloon drive section 6a detects that automatic control of the balloon 24*d* by the balloon control apparatus 6 is not turned on, based on an instruction signal outputted from the scope switch section 22*d* via the universal cord 23.

On the other hand, the balloon drive section 6*a* performs an air feeding operation according to an instruction from the computing section 6*b* instead of instruction signals outputted from the air feeding switch and the air exhaust switch in the scope switch section 22*d* if the balloon drive section 6*a* detects that automatic control of the balloon 24*d* by the balloon control apparatus 6 is turned on, based on an instruction signal outputted from the scope switch section 22*d* via the universal cord 23.

In other words, when an air feeding operation according to an instruction from the computing section 6*b* is underway, the balloon drive section 6*a* invalidates all of instructions according to operations of the air feeding switch and the air exhaust switch in the scope switch section 22*d*.

The computing section 6*b* is configured to neither perform computing nor provide instruction in relation to operation of the balloon drive section 6*a* if the computing section 6*b* detects that automatic control of the balloon 24*d* is not turned on, based on an instruction signal outputted from the scope switch section 22*d* via the universal cord 23.

Also, the computing section 6*b* is configured to, if computing section 6*b* detects that automatic control of the balloon 24*d* is turned on, based on an instruction signal outputted from the scope switch section 22*d* via the universal cord 23, obtain luminance information on an endoscopic image outputted from the image processing section 4*c* of the processor 4 and provide an instruction relating to an air feeding operation, which is performed by the balloon drive section 6*a*, according to a result of determination of whether or not the obtained luminance information meets a predetermined condition specified by threshold information read from the storage section 6*c*.

In the storage section 6*c*, threshold information for specifying a predetermined condition used for determination by the computing section 6*b* is stored in advance.

More specifically, in the storage section 6*c*, for example, a lower limit value TH1 and an upper limit value TH2 for a luminance value according to luminance information obtained by the computing section 6*b* are stored in advance as the threshold information.

Note that the lower limit value TH1 for the luminance value is set as a luminance value for a case where, for example, a brightness of an endoscopic image outputted from the image processing section 4*c* in the processor 4 becomes extremely low as a result of at least a part of the objective window 24*b* of the distal end portion 24 being in direct contact with tissues of e.g., an organ in the body cavity.

Also, the upper limit value TH2 for the luminance value is set as a luminance value for a case where, for example, a brightness of an endoscopic image outputted from the image processing section 4*c* of the processor 4 becomes extremely high as a result of illuminating light exiting from the illumination window 24*a* of the distal end portion 24 being reflected by tissues of, e.g., an organ in a body cavity, causing halation.

Next, an operation of the endoscope system 1 according to the present embodiment will be described.

First, a surgeon or the like powers on the respective parts of the endoscope system 1 with the respective connectors at the end portion of the universal cord 23 connected to the light source apparatus 3, the processor 4 and the balloon control apparatus 6. Then, along with the power-on of the respective parts of the endoscope system 1, acquisition of an endoscopic image by the endoscope 2, supply of illuminating light by the light source apparatus 3, image processing by the processor 4 and display of the endoscopic image by the display apparatus 5 are started, respectively.

Also, the surgeon or the like inserts the insertion portion 21 to a deep part in a body cavity of a subject by performing an insertion operation while viewing the endoscopic image displayed on the display apparatus 5.

Figure 2:
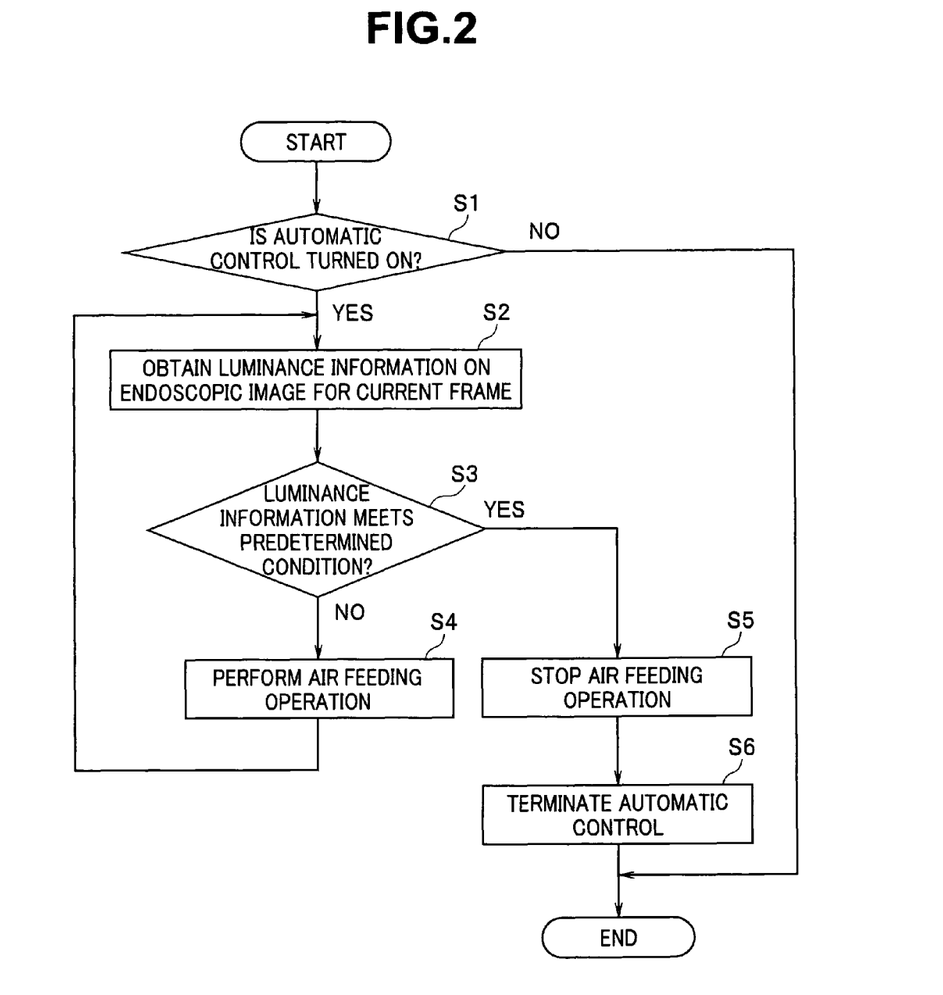
FIG. 2 is a flowchart illustrating an example of processing performed in a balloon control apparatus.
Figure 3:
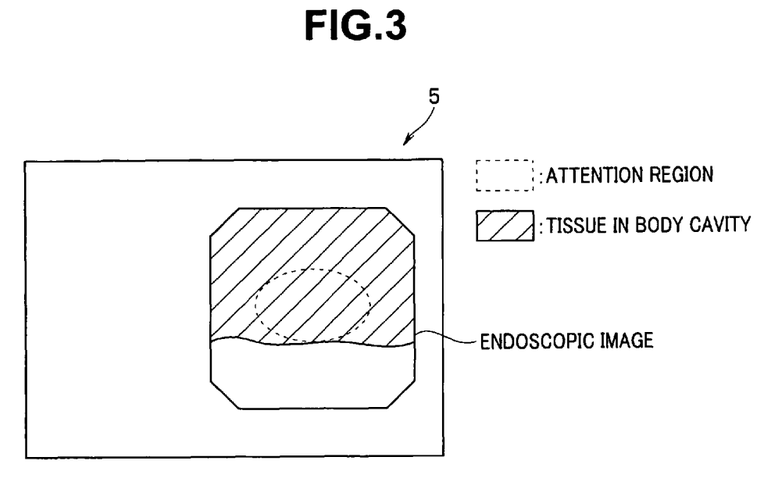
FIG. 3 is a diagram illustrating an example of an endoscopic image displayed on a display apparatus before performance of a series of processing steps in FIG. 2.
Figure 4:
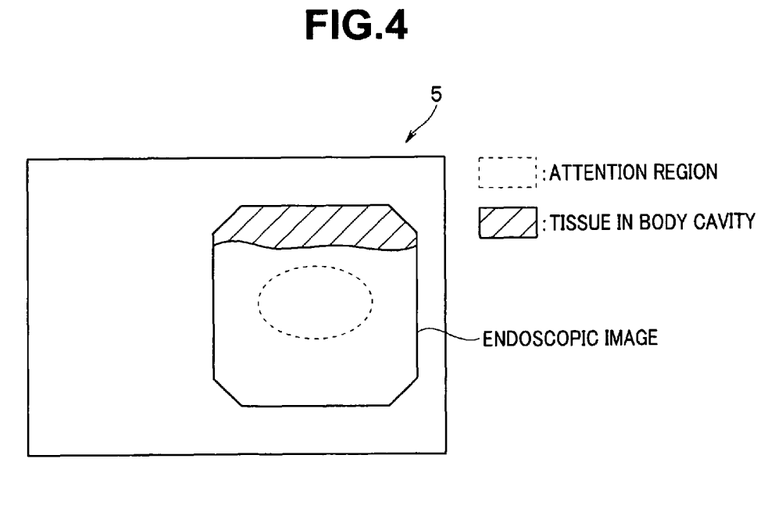
FIG. 4 is a diagram illustrating an example of an endoscopic image displayed on the display apparatus after performance of the series of processing steps in FIG. 2.

Here, processing, etc., performed in the balloon control apparatus 6 according to the present embodiment will be described with reference to FIGS. 2 to 4. FIG. 2 is a flowchart illustrating an example of processing performed in a balloon control apparatus. FIG. 3 is a diagram illustrating an example of an endoscopic image displayed on a display apparatus before performance of a series of processing steps in FIG. 2. FIG. 4 is a diagram illustrating an example of an endoscopic image displayed on a display apparatus after performance of the series of processing steps in FIG. 2.

If an endoscopic image such as illustrated in FIG. 3 is displayed on the display apparatus 5 because of intervention of tissues of, e.g., an organ in a body cavity between an attention region as a region corresponding to a destination of insertion of the insertion portion 21 or a region in which a target of treatment via a treatment instrument inserted from the forceps port 22*a* exists, and the distal end face of the distal end portion 24, the surgeon or the like operates the automatic control mode switch in the scope switch section 22*d* to provide an instruction to turn on automatic control of the balloon 24*d* by the balloon control apparatus 6.

The computing section 6*b* determines whether or not an instruction to turn on automatic control of the balloon 24*d* is provided, based on an instruction signal outputted from the scope switch section 22*d* via the universal cord 23 (step S1 in FIG. 2).

If the computing section 6*b* obtains a determination result that no instruction to turn on automatic control of the balloon 24*d* is provided in step S1 in FIG. 2, the computing section 6*b* neither performs an operation nor provides an instruction in relation to operation of the balloon drive section 6*a*. In other words, if a determination result that no instruction to turn on automatic control of the balloon 24*d* is provided is obtained as a result of the processing in step S1 in FIG. 2, the balloon 24*d* can be expanded or shrunk so as to enter a desired expansion state according to operations of the air feeding switch and the air exhaust switch in the scope switch section 22*d*.

If the computing section 6*b* obtains a determination result that an instruction to turn on automatic control of the balloon 24*d* is provided in step S1 in FIG. 2, the computing section 6*b* starts automatic control of the balloon 24*d* and performs processing for obtaining luminance information on an endoscopic image for a current frame, which is outputted from the image processing section 4*c* of the processor 4 (step S2 in FIG. 2).

More specifically, if the computing section 6*b* obtains a determination result that an instruction to turn on automatic control of the balloon 24*d* is provided in step S1 in FIG. 2, the computing section 6*b* calculates an average value AVG of luminance values of respective pixels existing in the endoscopic image for the current frame, which is outputted from the image processing section 4*c* of the processor 4, for example, for any one of R, G and B color components.

The computing section 6*b* determines whether or not the luminance information obtained in step S2 in FIG. 2 meets a predetermined condition specified by threshold information read from the storage section 6*c* (step S3 in FIG. 2).

More specifically, the computing section 6*b* reads, for example, a lower limit value TH1 for a luminance value and an upper limit value TH2 for a luminance value according to the average value AVG of the luminance values, which has been calculated in step S2 in FIG. 2, from the storage section 6c, and determines whether or not the average value AVG for the luminance values, which have been calculated by the processing in step S2 in FIG. 2, meets a magnitude relationship of TH1<AVG<TH2.

Then, if the computing section 6b obtains a determination result that the luminance information obtained in step S2 in FIG. 2 does not meet the predetermined condition in step S3 in FIG. 2, the computing section 6b provides an instruction to perform an air feeding operation to supply a predetermined amount of a gas to the balloon 24d to the balloon drive section 6a (step S4 in FIG. 2) and then returns to step S2 in FIG. 2 and performs the processing.

Also, if the computing section 6b obtains a determination result that the luminance information obtained in step S2 in FIG. 2 meets the predetermined condition in step S3 in FIG. 2, the computing section 6b provides an instruction to stop the air feeding operation to the balloon drive section 6a to terminate the automatic control of the balloon 24d (steps S5 and S6 in FIG. 2).

In the above-described series of processing steps, etc., relating to automatic control of the balloon 24d, the air feeding operation by the balloon drive section 6a is continued until an endoscopic image meeting the predetermined condition in step S3 in FIG. 2, such as indicated by the magnitude relationship of TH1<AVG<TH2 as an example, is outputted from the image processing section 4c of the processor 4. Also, in the above-described series of processing steps, etc., relating to automatic control of the balloon 24d, the air feeding operation by the balloon drive section 6a is stopped substantially immediately after an endoscopic image meeting the predetermined condition in step S3 in FIG. 2, such as indicated by the magnitude relationship of TH1<AVG<TH2 as an example, is outputted from the image processing section 4c of the processor 4.

In other words, according to the present embodiment, as a result of the series of processing steps, etc., relating to automatic control of the balloon 24d being performed, the balloon 24d is expanded to a degree that intervention of tissues of, e.g., an organ in a body cavity between an attention region and the distal end face of the distal end portion 24 is resolved and the tissues in the body cavity existing around the distal end portion 24 is excluded, enabling transition of a state of a region around the distal end portion 24 from a state in which the attention region cannot be viewed (see FIG. 3) to a state in which the attention region can be viewed (see FIG. 4). As a result, the present embodiment enables a field of view for observing or treating a desired site (including an attention region) to be ensured.

Note that the series of processing steps illustrated in FIG. 2 is not limited to a case where only one balloon is provided at the outer circumferential part of the distal end portion 24, and can be applied to a case where a plurality of balloons are provided at the outer circumferential part of the distal end portion 24, in such a manner that is substantially similar to the above.

Also, in the series of processing steps illustrated in FIG. 2, as long as respective values that enables determination of a case where a brightness of an endoscopic image outputted from the image processing section 4c of the processor 4 becomes extremely low and a case where the brightness of the endoscopic image becomes extremely high are stored in the storage section 6c in advance as threshold information, processing for obtaining a value other than the average value AVG of the luminance values as luminance information may be performed.

Figure 5:
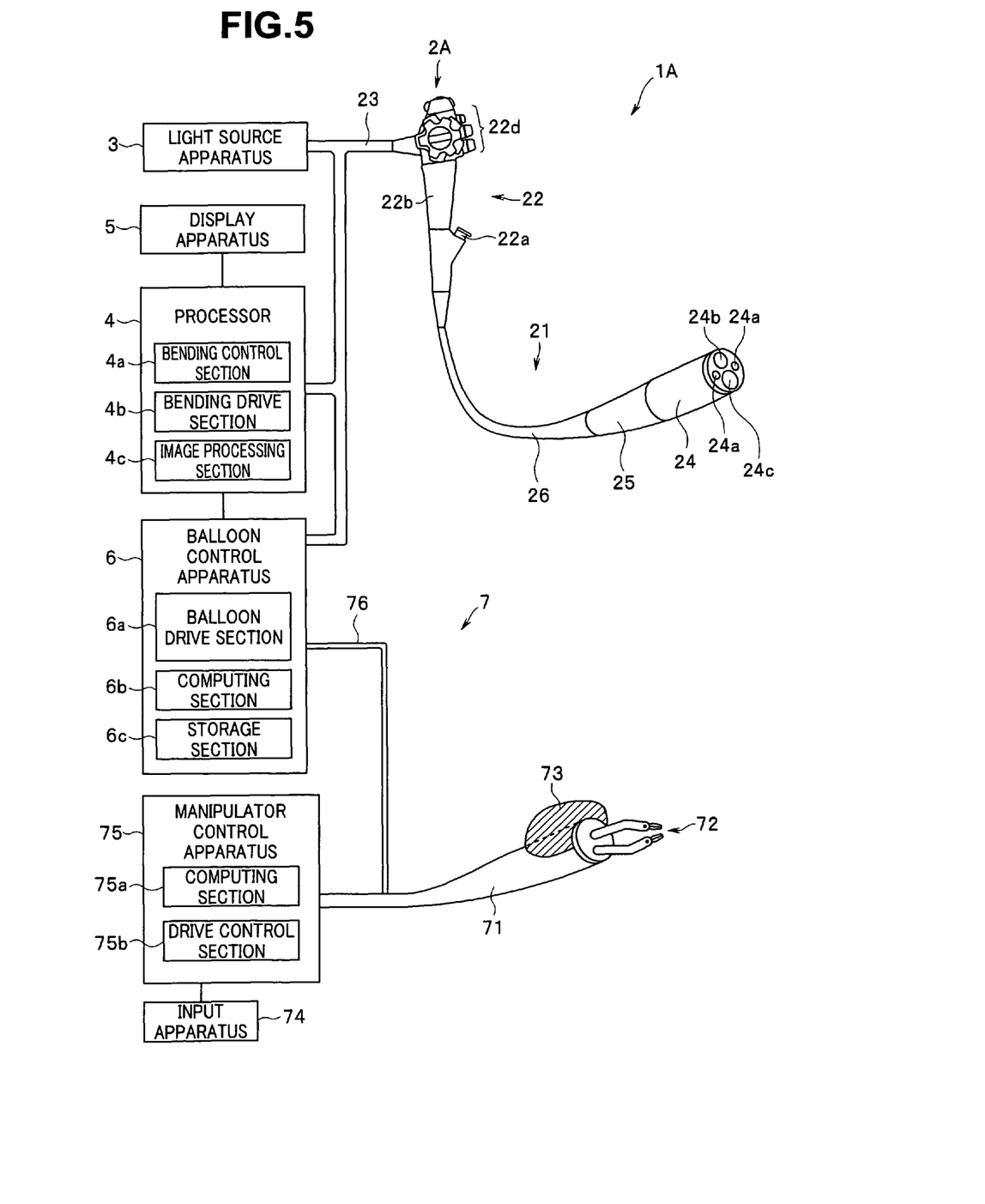
FIG. 5 is a diagram illustrating a configuration of a main part of an endoscope system according to a modification of the embodiment of the present invention.

Also, the series of processing steps illustrated in FIG. 2 is not limited to a case where a balloon is attached to a distal end portion of an endoscope such as illustrated in FIG. 1, and can be applied to a case where a balloon is attached to a distal end portion of a treatment instrument used in a state in which the treatment instrument is inserted inside an endoscope, for example, such as illustrated in FIG. 5, in such a manner that is substantially similar to the above.

Here, a configuration of an endoscope system 1A according to a modification of the present embodiment will be described with reference to FIG. 5. FIG. 5 is a diagram illustrating a configuration of a main part of an endoscope system according to a modification of the embodiment of the present invention.

Note that, hereinafter, for simplicity, a detailed description of parts having configurations or the like that are similar to those in the endoscope system 1 will be omitted and a description will be provided mainly on parts having configurations or the like that are different from those in the endoscope system 1.

As illustrated in FIG. 5, the endoscope system 1A includes: an endoscope 2A capable of picking up an image of an object in a body cavity of a subject to acquire an endoscopic image; a light source apparatus 3 having a function as a supply source of illuminating light for illuminating the object; a processor 4 that performs, e.g., image processing on the endoscopic image acquired by the endoscope 2A; a display apparatus 5 capable of displaying, e.g., the endoscopic image subjected to the image processing by the processor 4; a balloon control apparatus 6 that performs an operation relating to control of a balloon 73 (which will be described later); and a manipulator apparatus 7.

The endoscope 2A has a configuration substantially similar to the configuration of the endoscope 2 with the balloon 24d and the non-illustrated gas circulation duct (gas circulation channel), which is used for air feeding and air exhaust by the balloon control apparatus 6, removed.

The manipulator apparatus 7 includes a manipulator body 71, a grasping forceps section 72 provided at a distal end portion of the manipulator body 71, a balloon 73 provided in the vicinity of the grasping forceps section 72, at the distal end portion of the manipulator body 71, an input apparatus 74 that enables an operation of the grasping forceps section 72, and a manipulator control apparatus 75 that makes the grasping forceps section 72 operate according to an input operation via the input apparatus 74. Also, inside the manipulator body 71, a part of a tubular member 76 used for air feeding and air exhaust by the balloon control apparatus 6 is inserted.

The manipulator body 71 has an elongated shape that enables the manipulator body 71 to be inserted to a non-illustrated treatment instrument insertion duct (treatment instrument channel) from a forceps port 22a and enables the grasping forceps section 72 to project from a distal end opening portion 24c in a state in which the manipulator body 71 is inserted in the treatment instrument insertion duct.

The grasping forceps section 72 includes two grasping forceps configured to be able to pinch and grasp a target object by a grasping force according to drive control performed by the manipulator control apparatus 75. Also, for the two grasping forceps in the grasping forceps section 72, a plurality of non-illustrated actuators that operate so as to make the respective grasping forceps face in a direction according to the drive control performed by the manipulator control apparatus 75, respectively.

In other words, the grasping forceps section 72 having a function as a treatment section and is configured to enable treatment of a target site in a body cavity of a subject in a state in which the grasping forceps section 72 projects from a distal end face of the distal end portion 24.

The balloon 73 having a function as an exclusion section includes a material such as rubber, and is configured to expand upon supply of a gas to an inner space thereof and shrink upon discharge of the gas supplied to the inner space. Also, the inner space of the balloon 73 is in communication with one end portion of the tubular member 76 inserted inside the manipulator body 71. Note that the other end portion of the tubular member 76 is connected to a balloon drive section 6a of the balloon control apparatus 6. The input apparatus 74 includes, for example, a joystick, and is configured to capable of detecting an amount of input according to an input operation performed by a surgeon or the like and outputting the amount of input to the manipulator control apparatus 75.

The manipulator control apparatus 75 includes a computing section 75a and a drive control section 75b.

The computing section 75a is configured to calculate one or more control parameters for determining an orientation and a grasping force of each of the two grasping forceps in the grasping forceps section 72 based on a magnitude of the amount of input via the input apparatus 74.

The drive control section 75b is configured to drive the two grasping forceps in the grasping forceps section 72 based on the respective control parameters calculated by the computing section 75a.

Note that the endoscope system 1A according to the modification of the present embodiment is not limited to one configured with respective switches such as an automatic control mode switch, an air feeding switch and an air exhaust switch provided in a scope switch section 22d, and may be one configured with the respective switches provided in the input apparatus 74.

Next, an operation of the endoscope system 1A according to the modification of the present embodiment will be described.

First, a surgeon or the like connects respective connectors at an end portion of a universal cord 23 to the light source apparatus 3, the processor 4 and the balloon control apparatus 6, and powers on the respective parts of the endoscope system 1A with the other end portion of the tubular member 76 connected to the balloon control apparatus 6. Then, along with the power-on of the respective parts of the endoscope system 1A, acquisition of an endoscopic image by the endoscope 2A, supply of illuminating light by the light source apparatus 3, image processing by the processor 4 and display of the endoscopic image by the display apparatus 5 are started, respectively.

Also, the surgeon or the like inserts an insertion portion 21 until the insertion portion 21 reaches a desired site including a region in which a target of treatment via the grasping forceps section 72 exists by performing an insertion operation while viewing the endoscopic image displayed on the display apparatus 5.

If an endoscopic image such as illustrated in FIG. 3 is displayed on the display apparatus 5 because of intervention of tissues of, e.g., an organ in the body cavity between an attention region as the region in which a target of treatment via the grasping forceps section 72 exists and the distal end face of the distal end portion 24, the surgeon or the like operates the automatic control mode switch in the scope switch section 22d with the distal end portion of the manipulator body 71 projecting from the distal end opening portion 24c to provide an instruction to turn on automatic control of the balloon 73 by the balloon control apparatus 6.

The computing section 6b determines whether or not an instruction to turn on automatic control of the balloon 73 is provided, based on an instruction signal outputted from the scope switch section 22d via the universal cord 23 (step S1 in FIG. 2).

If the computing section 6b obtains a determination result that no instruction to turn on automatic control of the balloon 73 is provided in step S1 in FIG. 2, the computing section 6b neither performs an operation nor provides an instruction in relation to operation of the balloon drive section 6a. In other words, if a determination result that no instruction to turn on automatic control of the balloon 73 is provided is obtained as a result of the processing in step S1 in FIG. 2, the balloon 73 can be expanded or shrunk so as to enter a desired expansion state according to operations of the air feeding switch and the air exhaust switch in the scope switch section 22d.

If the computing section 6b obtains a determination result that an instruction to turn on automatic control of the balloon 73 is provided in step S1 in FIG. 2, the computing section 6b starts automatic control of the balloon 73 and performs processing for obtaining luminance information on an endoscopic image for a current frame, which is outputted from the image processing section 4c of the processor 4 (step S2 in FIG. 2).

More specifically, if the computing section 6b obtains a determination result that an instruction to turn on automatic control of the balloon 73 is provided in step S1 in FIG. 2, the computing section 6b calculates an average value AVG of luminance values of respective pixels existing in the endoscopic image for the current frame, which is outputted from the image processing section 4c of the processor 4, for example, for any one of R, G and B color components.

The computing section 6b compares the luminance information obtained in step S2 in FIG. 2 and threshold information read from the storage section 6c to determine whether or not the luminance information meets a predetermined condition according to the threshold information (step S3 in FIG. 2).

More specifically, the computing section 6b reads, for example, a lower limit value TH1 for a luminance value and an upper limit value TH2 for a luminance value according to the average value AVG of the luminance values, which has been calculated in step S2 in FIG. 2, from the storage section 6c, and determines whether or not the average value AVG for the luminance values, which have been calculated by the processing in step S2 in FIG. 2, meets a magnitude relationship of $TH1<AVG<TH2$.

Then, if the computing section 6b obtains a determination result that the luminance information obtained in step S2 in FIG. 2 does not meet the predetermined condition in step S3 in FIG. 2, the computing section 6b provides an instruction to perform an air feeding operation to supply a predetermined amount of a gas to the balloon 73 to the balloon drive section 6a (step S4 in FIG. 2) and then returns to step S2 in FIG. 2 and performs the processing.

Also, if the computing section 6b obtains a determination result that the luminance information obtained in step S2 in FIG. 2 meets the predetermined condition in step S3 in FIG. 2, the computing section 6b provides an instruction to stop the air feeding operation to the balloon drive section 6a to terminate the automatic control of the balloon 73 (steps S5 and S6 in FIG. 2).

In the above-described series of processing steps, etc., relating to automatic control of the balloon 73, the air feeding operation by the balloon drive section 6a is continued until an endoscopic image meeting the predetermined condition in step S3 in FIG. 2, such as indicated by the magnitude relationship of $TH1<AVG<TH2$ as an example, is outputted from the image processing section 4c of the processor 4. Also, in the above-described series of processing steps, etc., relating to automatic control of the balloon 73, the air feeding operation by the balloon drive section 6a is stopped substantially immediately after an endoscopic image meeting the predetermined condition in step S3 in FIG. 2, such as indicated by the magnitude relationship of TH1<AVG<TH2 as an example, is outputted from the image processing section 4c of the processor 4.

In other words, according to the modification of the present embodiment, as a result of the series of processing steps, etc., relating to automatic control of the balloon 73 being performed, the balloon 73 is expanded to a degree that intervention of tissues of, e.g., an organ in a body cavity between an attention region and the distal end face of the distal end portion 24 is resolved and the tissues in the body cavity existing around the distal end portion 24 is excluded, enabling transition of a state of a region around the distal end portion 24 from a state in which treatment of the attention region by the grasping forceps section 72 is impossible (see FIG. 3) to a state in which treatment of the attention region by the grasping forceps section 72 is possible (see FIG. 4). As a result, the modification of the present embodiment enables a field of view for observing or treating a desired site (including an attention region) to be ensured.

Note that the present embodiment and the modification described above are not limited to ones in which an average value of luminance values of respective pixels existing in an endoscopic image for a current frame is calculated as a value of AVG, and may be, for example, ones in which an average value of luminance values of respective pixels existing in an attention region in an endoscopic image for a current frame is calculated as a value of AVG.

The series of processing steps illustrated in FIG. 2 is not limited to a case where a balloon is provided at a distal end portion of an endoscope, and can be applied to, for example, a case where a retractor is provided at a distal end portion of an endoscope.

Figure 6:
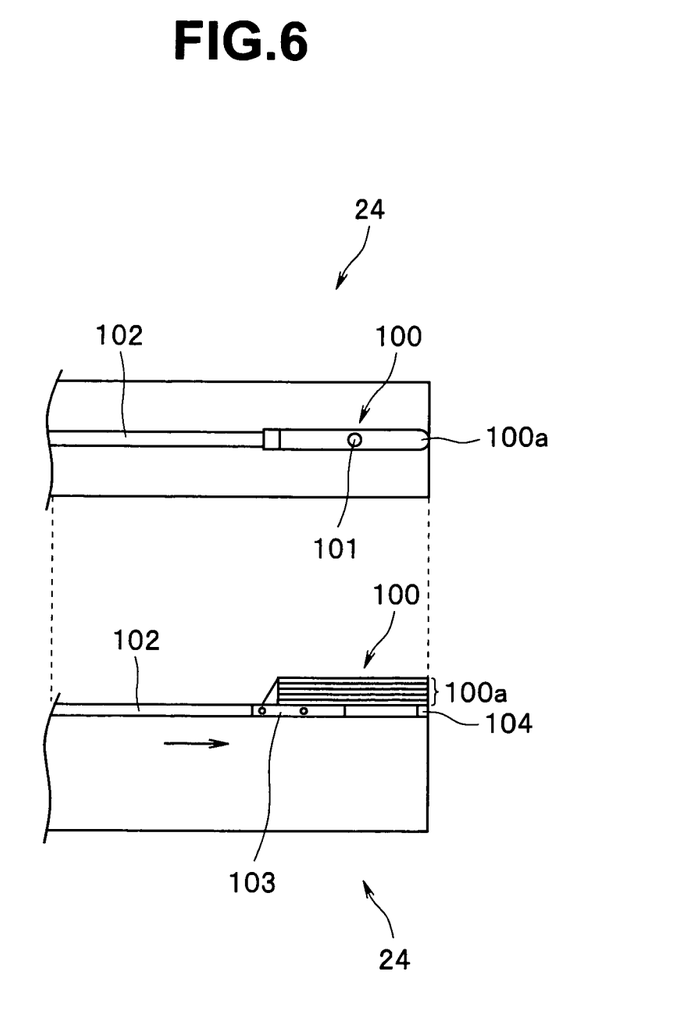
FIG. 6 is a diagram schematically illustrating an example of a configuration where a retractor is provided at a distal end portion of an endoscope.
Figure 7:
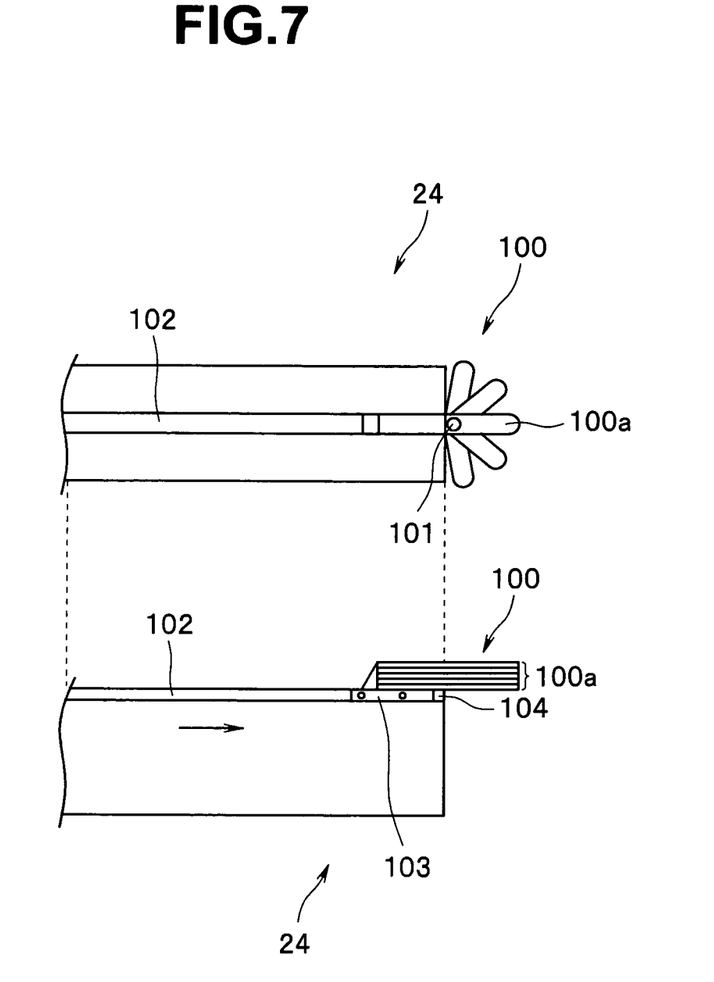
FIG. 7 is a diagram for describing a state in which the retractor in FIG. 6 is spread out.
Figure 8:
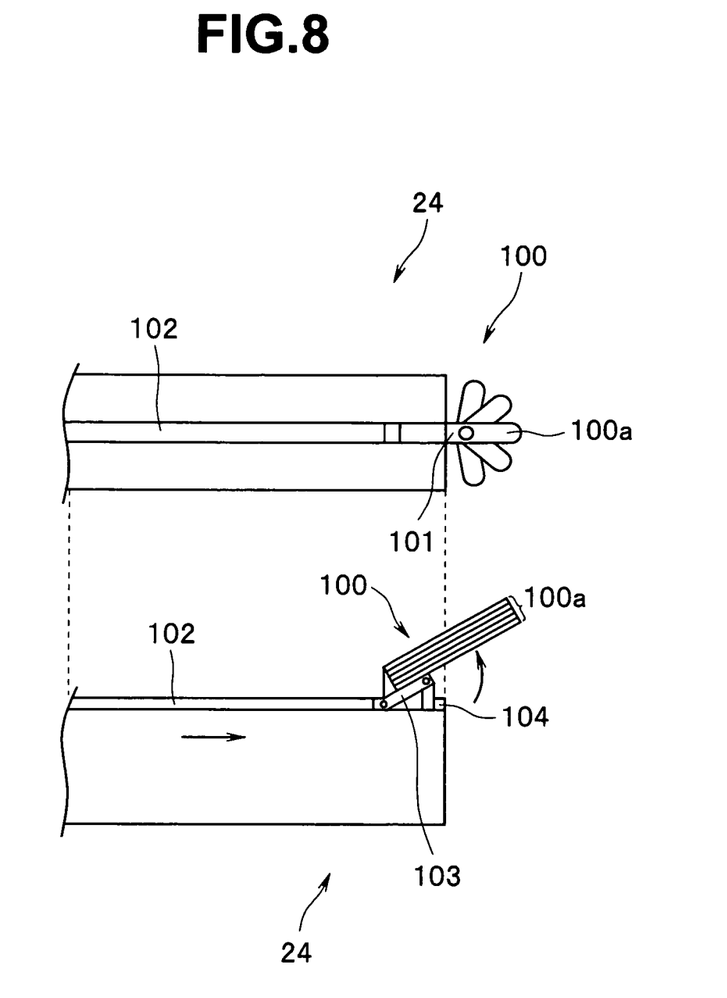
FIG. 8 is a diagram for describing a state in which the retractor in FIG. 6 is spread out and uplifted.

Here, a case where a retractor 100 such as illustrated in FIGS. 6 to 8 is provided at a distal end portion 24 instead of the balloon 24d will be described. FIG. 6 is a diagram schematically illustrating an example of a configuration where a retractor is provided at a distal end portion of an endoscope. FIG. 7 is a diagram illustrating a state in which the retractor in FIG. 6 is spread out. FIG. 8 is a diagram illustrating a state in which the retractor in FIG. 6 is spread out and uplifted.

As illustrated in FIG. 6, the retractor 100 includes a plurality of plate-shaped members 100a whose rear end portions are fixed to a flexion and deformation portion 103 by a shaft member 101, the flexion and deformation portion 103 being provided at a distal end portion of a base member 102 on which the retractor 100 is arranged.

Also, as illustrated in FIG. 6, the retractor 100 has a configuration in which when the base member 102 is not pushed in at all, the plurality of plate-shaped members 100a are housed at a predetermined position in a distal end portion 24 with the plate-shaped members overlapped with one another.

Also, as illustrated in FIG. 7, the retractor 100 has a configuration in which when the base member 102 is pushed in to a degree that the flexion and deformation portion 103 abuts a stopper 104 on the distal end side, the plurality of plate-shaped members 100a spread out in a fan-like form with the shaft member 101 as a center.

Also, as illustrated in FIG. 8, the retractor 100 has a configuration in which when the base member 102 is further pushed in with the flexion and deformation portion 103 abutting the stopper 104, the flexion and deformation portion 103 is flexed and thereby deforms, whereby the plurality of plate-shaped members 100a spread out (in a fan-like form) with the shaft member 101 as a center and uplifted.

In other words, if the retractor 100 is provided at the distal end portion 24 instead of the balloon 24d, the series of processing steps in FIG. 2 can be applied by changing the configuration of, e.g., the balloon control apparatus 6 to change the air feeding operation in step S4 in FIG. 2 to an operation to push the base member 102 in.

Figure 9:
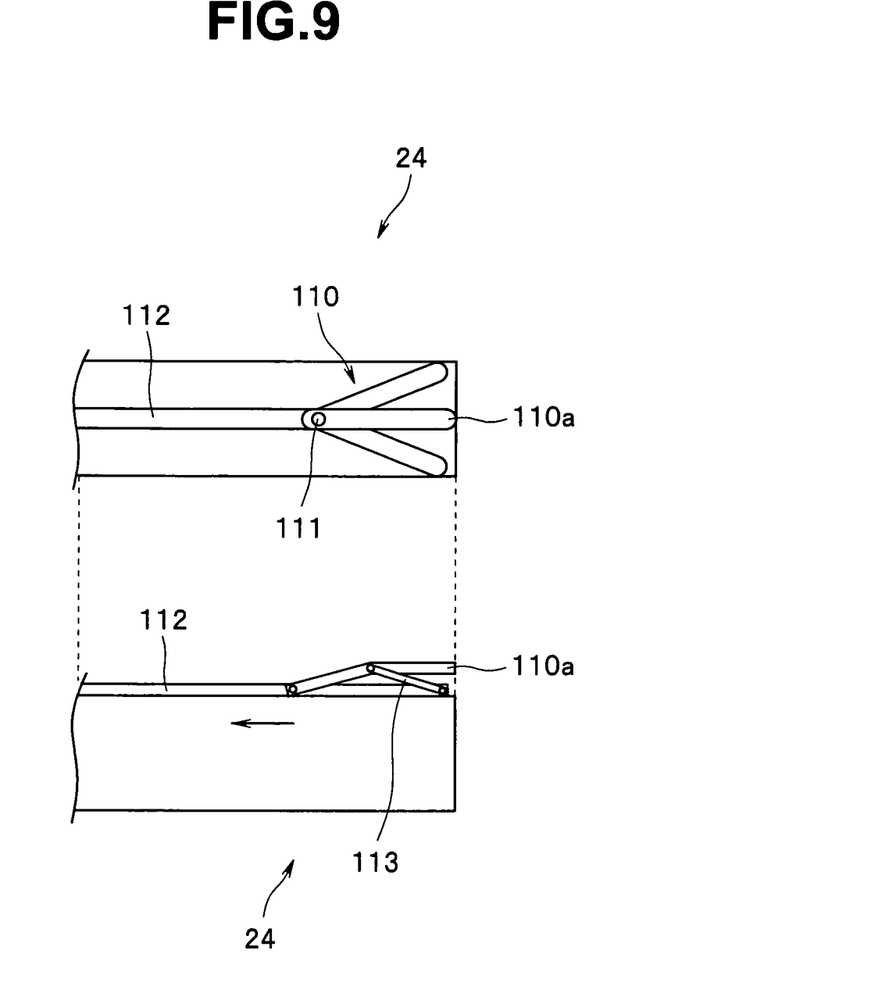
FIG. 9 is a diagram schematically illustrating an example of a configuration where a retractor is provided at a distal end portion of an endoscope, which is different from that in FIG. 6.
Figure 10:
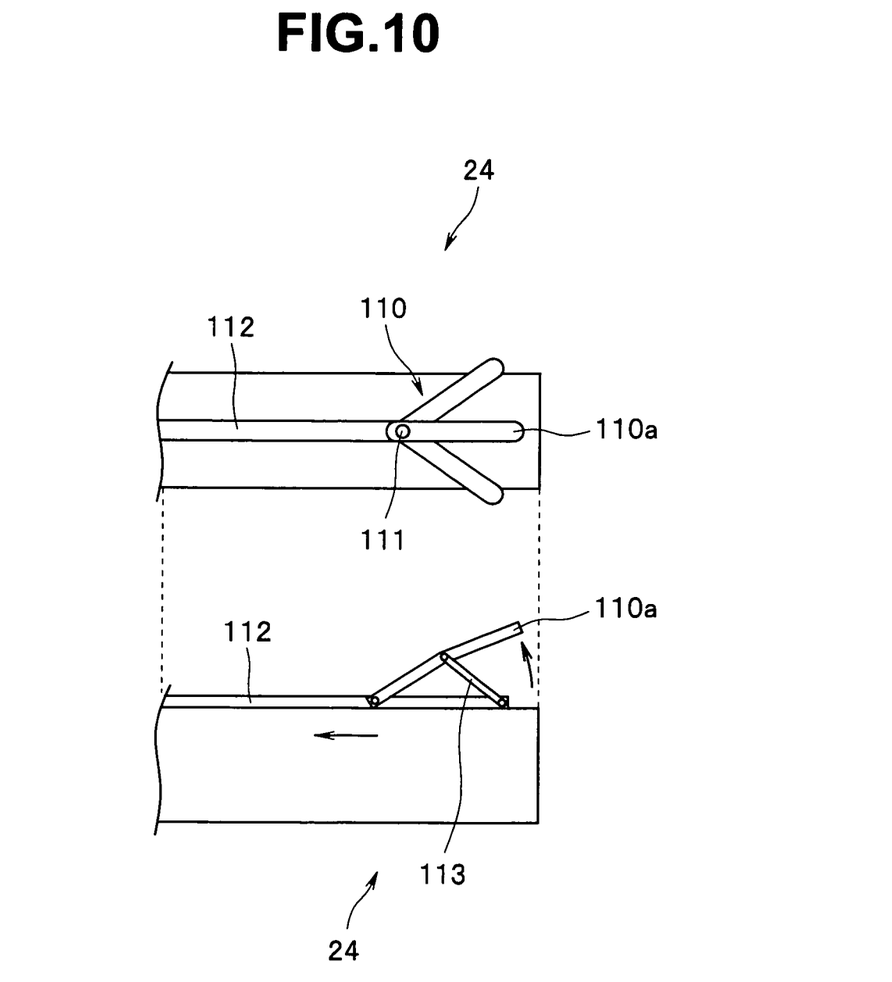
FIG. 10 is a diagram for describing a state in which the retractor in FIG. 9 is spread out.

Next, a case where a retractor 110 such as illustrated in FIGS. 9 and 10 is provided at the distal end portion 24 instead of the balloon 24d will be described. FIG. 9 is a diagram schematically illustrating an example of a configuration where a retractor is provided at a distal end portion of an endoscope, which is different from the example in FIG. 6. FIG. 10 is a diagram illustrating a state in which the retractor in FIG. 9 is spread out.

As illustrated in FIG. 9, the retractor 110 includes a plurality of plate-shaped members 110a whose rear end portions are fixed to a predetermined position in a base member 112 via a shaft member 111. Also, as illustrated in FIG. 9, a part at a certain position of the plate-shaped members 110a and a distal end portion of the base member 112 are connected via a connection member 113.

Also, as illustrated in FIG. 9, the retractor 110 has a configuration in which when the base member 112 is not pulled toward the rear end side at all, the plurality of plate-shaped members 110a are housed at a predetermined position in the distal end portion 24 with the plate-shaped members 110a substantially folded.

Also, as illustrated in FIG. 10, the retractor 110 has a configuration in which as the base member 112 is pulled toward the rear end side, the plurality of plate-shaped members 110a spread out in a fan-like form with the shaft member 111 as a center and uplifted by the connection member 113.

In other words, in a case where the retractor 110 is provided at the distal end portion 24 instead of the balloon 24d, the series of processing steps in. FIG. 2 can be applied by changing the configuration of, e.g., the balloon control apparatus 6 to change the air feeding operation in step S4 in FIG. 2 to an operation to pull the base member 112.

Note that the present invention is not limited to the embodiment, the modification and the like described above and it should be understood that various alterations and applications are possible without departing the spirit of the invention.

What is claimed is:
1. A medical system comprising:
an endoscope including an insertion portion that can be inserted into a body cavity of a subject, an image pickup section provided at a distal end portion of the insertion portion, an objective window provided at the distal end portion and that allows an image of an object that is picked up by the image pickup section to enter the endoscope, and an illumination window provided at the distal end portion and that allows illuminating light for illuminating the subject to exit the endoscope;
an exclusion section configured to, when the insertion portion is inserted into the body cavity of the subject, exclude a tissue existing around the distal end portion;
a computing section that obtains an average value of luminance values of respective pixels of the image picked up by the image pickup section, and determines whether or not the obtained average value of the luminance values falls within a predetermined range that is specified between (i) luminance information in a case where halation is caused by the illuminating light reflected by a tissue in the body cavity and (ii) luminance information in a case where the objective window and the tissue are in direct contact with each other; and a drive section that, if the computing section obtains a determination result that the average value of the luminance values does not fall within the predetermined range, continues an operation to drive the exclusion section, and if the computing section obtains a determination result that the average value of the luminance values falls within the predetermined range, stops the operation to drive the exclusion section.

2. The medical system according to claim 1, wherein the predetermined range is specified by a first luminance value obtained when the objective window and the tissue in the body cavity are in direct contact with each other and a second luminance value obtained when the illuminating light causes halation as a result of the illuminating light being reflected by the tissue.

3. The medical system according to claim 2, wherein in a case where the first luminance value is $TH1$, the second luminance value is $TH2$, and the average value obtained by the computing section is $AVG$, if a determination result that a magnitude relationship of $TH1<AVG<TH2$ is not met is provided by the computing section, the drive section continues the operation to drive the exclusion section, and if a determination result that the magnitude relationship of $TH1<AVG<TH2$ is met is provided by the computing section, the drive section stops the operation to drive the exclusion section.

4. The medical system according to claim 1, further comprising a switch that enables provision of an instruction for turning on automatic control of the exclusion section, wherein if the drive section detects that the instruction is outputted from the switch, the drive section operates so as to drive the exclusion section based on the determination result provided by the computing section.

5. The medical system according to claim 1, further comprising:
a bending operation portion configured to enable a bending operation for bending a bending portion of the insertion portion;
a bending control section that calculates a bending amount according to the bending operation performed via the bending operation portion, and that performs control according to the calculated bending amount; and
a bending drive section that bends the bending portion according to the control performed by the bending control section.

6. The medical system according to claim 1, further comprising a treatment instrument configured to be inserted into a duct provided in the insertion portion, wherein the treatment instrument includes a treatment section that enables treatment of a target site in the body cavity of the subject with the treatment section projecting from a distal end face of the distal end portion, and the exclusion section provided in a vicinity of the treatment section.

* * * * *